(12) United States Patent
Mitani et al.

(10) Patent No.: US 7,191,037 B2
(45) Date of Patent: Mar. 13, 2007

(54) METHOD FOR CONTROLLING PRODUCTION PROCESS

(75) Inventors: Toshiharu Mitani, Yamaguchi (JP);
Masami Tsuruoka, Yamaguchi (JP);
Yasuo Miyoshi, Yamaguchi (JP)

(73) Assignee: Mitsui Chemicals, Inc., Tokyo (JP)

( * ) Notice: Subject to any disclaimer, the term of this patent is extended or adjusted under 35 U.S.C. 154(b) by 558 days.

(21) Appl. No.: 10/089,680

(22) PCT Filed: Aug. 6, 2001

(86) PCT No.: PCT/JP01/06724

§ 371 (c)(1),
(2), (4) Date: Apr. 3, 2002

(87) PCT Pub. No.: WO02/12969

PCT Pub. Date: Feb. 14, 2002

(65) Prior Publication Data

US 2003/0028355 A1    Feb. 6, 2003

(30) Foreign Application Priority Data

Aug. 7, 2000   (JP) .............................. 2000-244026

(51) Int. Cl.
*G05B 21/00* (2006.01)
*G05B 13/00* (2006.01)
*G05B 15/00* (2006.01)
*G01M 1/38* (2006.01)
*G05D 23/00* (2006.01)

(52) U.S. Cl. ..................... 700/268; 700/266; 700/275; 422/50; 422/52; 422/55; 422/62; 422/63; 422/67; 422/68.1; 422/81; 422/82.05; 422/82.09; 436/43; 436/164; 436/171; 436/172; 73/1.01; 73/1.02; 73/23.2; 73/23.35; 73/23.36; 73/23.37; 356/51 G

(58) Field of Classification Search ................ 700/266, 700/275, 268; 422/50, 52, 55, 62, 63, 67, 422/68.1, 81, 83, 82.05, 82.09; 436/43, 164, 436/171, 172; 73/1.01, 1.02, 23.2, 23.35, 73/23.36, 23.37; 356/51

See application file for complete search history.

(56) References Cited

U.S. PATENT DOCUMENTS

| | | | |
|---|---|---|---|
| 4,800,279 A * | 1/1989 | Hieftje et al. ............ | 250/339.09 |
| 5,121,337 A * | 6/1992 | Brown ..................... | 702/28 |
| 5,490,085 A * | 2/1996 | Lambert et al. ........... | 700/266 |
| 5,604,132 A * | 2/1997 | Capuano et al. ........... | 436/52 |
| 5,696,580 A * | 12/1997 | Kubo et al. ............... | 356/72 |
| 5,740,073 A * | 4/1998 | Bages et al. ............... | 702/30 |
| 5,796,476 A * | 8/1998 | Wang et al. ............... | 356/301 |
| 6,072,576 A * | 6/2000 | McDonald et al. ......... | 356/300 |
| 6,103,934 A * | 8/2000 | Hallinan et al. ........... | 562/517 |
| 6,115,673 A * | 9/2000 | Malin et al. ............... | 702/23 |
| 6,144,897 A * | 11/2000 | Selliers .................... | 700/269 |
| 6,820,013 B1 * | 11/2004 | Frickel et al. ............. | 702/25 |

FOREIGN PATENT DOCUMENTS

| | | |
|---|---|---|
| EP | 0 801 299 A1 | 10/1997 |
| JP | 6-259103 | 9/1994 |
| JP | 6-274228 | 9/1994 |
| JP | 11-12211 | 1/1999 |
| JP | 01112211 | 1/1999 |
| JP | 2000-140619 A | 5/2000 |
| WO | WO 97/49977 | 12/1997 |

OTHER PUBLICATIONS

European Patent Office, Application No. 019454449.3-2204. International Application No. PCT/JP01/06724. Applicant: Mitsui Chemicals, Inc. European Search Report, pp. 1-3. Mar. 20, 2006.

* cited by examiner

*Primary Examiner*—Brian Sines
(74) *Attorney, Agent, or Firm*—Buchanan Ingersoll & Rooney PC

(57) ABSTRACT

A method for controlling production process by performing near-infrared absorptiometric analysis by simple procedures in an accurate manner, in which control of production process step can be realized at a high accuracy by simple operation based on the thereby obtained analytical results, the said method comprising taking each absorbance spectrum for a plurality of standard samples in an analysis range including near-infrared region, calculating the average intensity and standard deviations for each of selected wave lengths to construct a data base, taking an absorbance spectrum in the said analysis range for each of analysis samples and comparing it with the data base in order to judge whether or not the intensity of the absorbance spectrum is within an assumed tolerance limit determined based on the stored standard deviations of the standard samples in the data base to thereby obtain control data by comparing, when wave lengths at which the observed intensity is outside the tolerance limit are present, these extraneous wave lengths with the production information given preliminarily in the data base, these control data being inputted to the production process step, so as to obtain production product within the above tolerance limit.

20 Claims, 12 Drawing Sheets

METHOD FOR CONTROLLING PRODUCTION PROCESS

FIELD OF THE INVENTION

The present invention relates to a method for controlling production process by controlling operation of production process steps by analyzing samples by a near-infrared absorptiometric analysis (near-infrared spectrochemical analysis).

BACKGROUND OF THE INVENTION

For analyzing chemical substances, foods, agricultural products and so on, near-infrared absorptiometric analysis has been in practical application. Using the resulting analytical data, control of production process for such substances may be realized. In the field of chemical industry, it has been proposed to realize control of operation of a production plant for chemical product by using data of near-infrared absorptiometric analyses of the raw materials, solvents, moisture content, intermediate products, final product, by-products and so on. In conventional near-infrared absorptiometric analysis, a near-infrared absorbance spectrum in a specific range (in the following, denoted sometimes as near-infrared spectrum) is taken and, based on a specific combination of absorbances at specific wave lengths included in this spectrum, the components, characteristic properties and so on to be determined are calculated by having resort to a preliminarily prepared calibration curve, in order to derive analysis values (predicted values).

In one generalized example of practicing the near-infrared absorptiometric analysis, a correlation equation (calibration curve) is prepared by absorbance spectra in a wave length range exhibiting a correlation obtained by near-infrared absorptiometry and analytical results obtained by conventional analysis practice, in order to presume the prospective quantitative analysis value. This analysis value is only a predicted value calculated using the calibration curve.

A near-infrared absorptiometry accompanies an inherent defective characteristic feature that there occurs a shift of the spectrum due to influences by, for example, moisture content and temperature of the objective material. This spectrum shift may behave as if there is an alteration in the concentration of the component or in another material property of the material to be observed, even if there is in fact no such alteration. When operation of a plant is carried out based on such false results, the resulting product will have an extra-rated quality.

By a near-infrared absorptiometry, a definite absorbance spectrum can be obtained steadily for a specific component under a definite observation condition and with specific material properties, while the absorbance spectrum may subject to deviation in the height or position of absorbance peak due to alteration in the condition, such as concentration, particle size and temperature, or may vary due to interference with the absorption peaks for co-existing extraneous components. From a near-infrared absorbance spectrum, which includes, as mentioned above, information for a plurality of constituent components, a calibration curve (correlation equation) for each component is prepared by means of a statistic technique, on the basis of which analysis is attained.

For the preparation of the calibration curve, samples each having a definite composition and definite characteristic features are taken and are subjected to conventional chemical analysis and to a near-infrared absorptiometric analysis, whereupon a correlation equation is derived by means of a statistic technique, such as a multiple linear regression analysis (MLR) or a partial least-squares method (PLS). A near-infrared absorbance spectrum includes a number of absorbance peaks, so that use of too many descriptive variables (assigned wave lengths) may result in reduction in the reliability due to overfitting of calibration curves. For this reason, there are used in general 2 to 5 descriptive variables for MLR and about ten descriptive variables for PLS.

It is a common practice for detecting the component concentrations and material properties using a wave length range of near-infrared region from 800 to 2,500 nm, that predicted values are estimated by selecting near-infrared spectral wave lengths each having a correlation with the results determined using conventional analysis apparatus or conventional material property observing apparatus under preparation of a correlation equation to obtain a predicted value of near-infrared analysis. However, the so-estimated predicted values represent only informations derived using the calibration curve prepared from values for limited wave lengths in numbers of 2–5 or about 10 selected within the wide near-infrared region of from 800 nm to 2,500 nm. Therefore, it is difficult by such a common practice to grasp the entire aspects or a delicate variation of a sample (or a product) and such a practice is not effective, in particular, in the case where preparation of calibration curve is not possible. Namely, it is difficult to prepare a calibration curve in the following cases:

(1) Variation of the parameter to be detected, such as concentration or material properties, is little.

(2) Temporal change of the sample occurs.

The object of the present invention is to provide a method of controlling production process capable of controlling the production process steps by a simple manner at a higher accuracy based on the result of analysis performed by a near-infrared absorptiometry without using calibration curve.

DISCLOSURE OF THE INVENTION

The present invention relates to the following method for controlling production process:

(1) A method for controlling production process without having resort to preparation of a calibration curve comprising taking an absorbance spectrum for each of a plurality of standard samples collected from a production process step in an analysis range including near-infrared region, constructing a data base from a differentiation curve of a near-infrared spectrum chart obtained using a plurality of production products that had been judged by conventional chemical analysis to be rated products, by calculating standard deviations and the average intensity of the standard samples (standard average intensity) in respect of each of the wave lengths selected from the spectrum included in the said analysis range at a constant interval, taking an absorbance spectrum in the said analysis range for each analysis sample collected from the production process step and comparing the resulting absorbance spectrum with the data base, estimating deviation (analysis deviation) of the intensity of the absorbance spectrum of each of the analysis samples (analysis intensity) at each of the said selected wave lengths from the standard average intensity, comparing, when the absorbance spectrum includes wave length(s) at which the analysis deviation of the absorbance spectrum of the analysis sample is outside a tolerance limit determined based on the standard deviation, the wave length showing the analysis deviation of the absorbance outside the tolerance limit with production information given preliminarily in the data base in order to find out one or more control factors responsive to the analysis deviation of absorbance of the analysis sample, estimating control data for reclaiming the production process based on the one or more control factors, and controlling the production process so as to obtain production product within the tolerance limit by inputting the said control data to the production process step.

(2) The method as defined in the above (1), wherein the production information stored in the data base are those of the component material corresponding to the said selected wave lengths.

(3) The method as defined in the above (1) or (2), wherein the deviations (analysis deviations) of the analysis intensities from the standard average intensity are discriminated as to whether or not they are within the tolerance limit determined based on the standard deviations given in the data base for the standard samples.

(4) The method as defined in any one of the above (1) to (3), wherein the said analysis range is from 400 nm to 2,500 nm.

(5) The method as defined in the above (4), wherein the said analysis is from 800 nm to 2,500 nm.

(6) The method as defined in any one of the above (1) to (5), wherein the selected wave lengths have an interval of 10 nm or less.

(7) The method as defined in the above (6), wherein the selected wave lengths have an interval of 2 nm or less.

(8) The method as defined in any one of the above (1) to (7), wherein the absorbance spectrum is processed by differentiation for the analysis samples.

(9) The method as defined in the above (8), wherein the absorbance spectrum is processed by building up the second derivative thereof.

(10) The method as defined in any one of the above (1) to (9), wherein the data base is constructed from a plurality of standard samples of a plurality of kinds, by calculating the standard average intensity and standard deviations for each kind.

(11) The method as defined in any one of the above (1) to (10), wherein absorbance spectra are obtained for a plurality of the analysis samples and estimating the deviations of average intensities of the analysis samples (analysis average intensity) at the selected wave lengths from the standard average intensity.

Production processes to be controlled by the present invention include processes for producing chemical products, foods and other products. A particular preference is given to processes for producing chemical products, such as for example, polyolefins, polyesters and phenols. According to the present invention, analysis samples collected from the raw materials, solvents, water content, intermediate products, production product, by-products and so on are analyzed by near-infrared absorptiometry to obtain observed values for these components and for material properties and, based on these observed values, the amounts of raw materials, solvent and water to be supplied to the production process, the production conditions, such as temperature, pressure and others, and so on are controlled so as to obtain the product having a predetermined quality.

By the analysis technique by near-infrared absorptiometry according to the present invention, absorbance spectrum is taken in an analysis range including near-infrared region from a plurality of standard samples collected from production process steps. The absorbance spectrum of standard sample is taken for each of a plurality of samples for each kind collected from production process steps for intermediate products and final product which have been judged to be rated product. Here, the word "each kind" means that sorted by the difference in the components, material properties and so on determined for each grade of manufacture. In accordance with such difference, the production condition varies also. According to the present invention, it is favorable to collect a plurality of standard samples for each kind and to take an absorbance spectrum for each of them. While a more accurate analysis can be attained as the number of samples increases, a number of samples of about 20 to 30 for each kind may be practical in general.

The analysis range in near-infrared region lies from 800 to 2,500 nm, wherein the range may be comprised of a part thereof or may comprise further a visible light region and/or a infrared region in addition to the near-infrared region. When it comprises visible light region and an infrared region, it may range from 400 to 2,500 nm. While the near-infrared region includes informations concerning the components and the material properties of the sample, the visible light region includes informations concerning colors thereof, so that it is preferable that the analysis range includes a visible light region when analysis and control concerning the color of the product are performed. While the absorbance spectrum may favorably be taken by observing the absorbance intensity continuously for the analysis range mentioned above, it is also permissible to prepare an absorbance spectrum by observing the absorbance intensities at selected wave lengths, as described in the following.

According to the present invention, average intensity (standard average intensity) and standard deviations for selected wave lengths selected from the absorbance spectrum obtained as above are calculated, from which a data base is constructed. It is favorable for the selected wave lengths to select a plurality of wave lengths each held at an interval therebetween, in particular, at a constant interval. The interval of the selected wave lengths may be 10 nm or less, preferably 2 nm or less. While the selected wave lengths may favorably be selected among all over the analysis range, it is permissible, when unnecessary part is present, to exclude such a part. The standard average intensity is determined preferably by averaging algebraically the intensities of the absorbance spectra of standard samples at each selected wave length for each kind and the standard deviations are determined favorably by calculation from the deviation of each intensity from the standard average intensity.

While the calculations of the standard average intensity and of the standard deviations may be carried out directly for the original spectrum obtained from the standard specification, it is preferable to carry out the calculation from differentiation-treated, in particular, second order differentiation-treated absorbance spectrum. The baseline of a near-infrared spectrum chart tends to rise up on the side of longer wave length due to influences by moisture content and so on and exhibits overlaps of spectral peaks. In contrast, the differentiation-treated spectrum has flat horizontal baseline. In particular, in the second derivative of the spectrum, the peaks are inverted with sharpened reproduction of lower peaks and the overlapped peaks become separated in a favorable manner. The average intensity and the standard deviations are determined using such differentiation-treated spectrum and are inputted into a computer to construct a data base. Such data base is built up for each kind of the standard samples.

The analysis samples are analyzed using the data bases obtained as above. The analysis samples are collected from the production process steps. For analyzing these analysis samples and, in particular, for discriminating as to whether or not they are rated product, absorbance spectra are taken for an analysis range, which are compared with the data base. Here, deviations (analysis deviations) of the intensities of absorbance spectra (analysis intensities) of the analysis samples from the standard average intensity are determined. Here, the discrimination is effected as to whether the analysis deviation is within a tolerance limit determined based on the standard deviation ($\sigma$) stored in the data base (for example, a value of $\sigma$, $2\sigma$ or $3\sigma$) or not, wherein the case of being within the tolerance limit can be judged as rated and the case of being outside can be judged as extra-rated.

It is permissible to collect and analyze only one single analysis sample or a plurality of analysis samples. In the case of the latter, the comparison with the data base may be performed each individually or by determining an average intensity for each of the selected wave lengths and comparing this with the standard average intensity. In case where the standard average intensity and standard deviations are determined for the standard samples for differentiation-treated absorbance spectra and are recorded in the data base, the comparison is made for the intensities of differentiation-treated absorbance spectra (including second order differentiation-treated ones) also for the analysis samples.

When the intensities of the absorbance spectra of the analysis samples are compared with the data base, the product can be judged as rated if the analysis deviation of the absorbance spectrum in an estimation range included in the analysis range is within the tolerance limit, for example, $3\sigma$, and be judged as extra-rated if it is outside the tolerance limit. While the estimation range may be identical with the analysis range, it may be a part thereof. For example, it is possible that the estimation may be effected only in the near-infrared region even if the absorbance spectrum is taken over the analysis range ranging from a visible light region to the near-infrared region. The practical manner of estimation in the estimation region may be decided voluntarily. The manner of estimation can be decided in accordance with each specific purpose of the analysis. For example, it is possible to judge as extra-rated when even one single analysis result of outside of the tolerance limit occurs for specific wave lengths or to judge as extra-rated when occurrence of outside of the tolerance limit in examination of a plurality of analysis samples reaches a predetermined proportion or higher. The judgement whether the result is within the tolerance limit or not may be made simply by comparing the intensity of the absorbance spectrum with the tolerance limit individually, while the judgement may be made by determining values equivalent to the deviation and so on and comparing them with the data base.

Since the absorption peaks of absorbance spectrum represent informations for, for example, composition of the analysis sample, material properties and so on, control of the production process can be realized so as to obtain the final product within the tolerance limit, if one or more wave lengths showing the extraneous intensity (analysis deviation) are present, by comparing such wave length(s) with the production information(s) recorded in the data base to obtain control data and inputting this control data to the production process step. For example, when such wave length for the extraneous intensity concern a specific component, this means that the component is present in an amount either in excess or in short of the standard amount. Therefore, control of the production process can be realized here by decreasing or increasing the amount of this component by inputting a control data therefor to the production process step so as to obtain the absorbance spectrum within the tolerance limit. When an unnecessary by-product is formed in an amount exceeding the tolerance limit therefor, a control data for attaining such a condition that no such by-product is formed may be obtained, in order to be inputted to the production process step. Concerning the material properties of the production product and other conditions, similar practice may be applied.

The production informations as described above are stored preliminarily in the computer as a data base. The absorption peaks of the near-infrared absorbance spectrum represent compositely the informations for the production process, such as the composition, material properties and so on, in which certain conditions, for example, the informations for a specific component and for others, are also represented by a combination of a plurality of absorption peaks. If the control data are recorded in the data base for the wave lengths at these absorption peaks, it is made possible, in the case where an analysis sample shows abnormal peaks outside the tolerance limit occur, to discriminate which condition or conditions is or are the origin of such abnormality, by comparing the wave lengths at such abnormal peaks with the data base. When, in this case, a control data for regaining the normal condition is inputted together with the discriminated production condition, the production process can be turned back to the normal operation by inputting the control data as such to the production process step.

In the near-infrared absorptiometric analysis and the method for controlling production processes described above, it is not necessary to prepare a calibration curve for each element for the analysis and the control of, for example, constituent components, material properties and so on, of each analysis sample and to carry out qualitative analysis thereof but is able to judge whether the product is rated or extra-rated, by simply discriminating as to whether the absorbance spectral intensities at selected wave lengths in the analysis range are within or without the tolerance limit by comparing the absorbance spectra at the selected wave lengths with the data base, whereby it is made possible to regain the normal operation of the production process by performing control of the process using the results obtained. Here, the operation for effecting the control of the process or of the analysis is simplified, since any qualitative estimation of the constituent components and of the material properties can be dispensed with. The accuracy of analysis is increased and correction of the calibration curve is unnecessary, since no calibration curve requiring accuracy is used. By using as the standard samples those which have been approved to be rated, by conventional chemical analysis, the analysis accuracy can be increased. While supplement of the data bases may be excluded, construction of the data base from more standard samples may facilitate increase in the analysis accuracy.

By the near-infrared absorptiometric analysis as described above, the analysis can be attained at a high accuracy by a simple procedure without necessitating to use any calibration curve, since the average value of the near-infrared absorbance intensities and the standard deviations of the standard samples at selected wave lengths are recorded in the data base and the absorbance spectra of the analysis samples are compared with the data base.

By the method for controlling production processes according to the present invention, control of the production processes can be realized based on the analytical results obtained as above, by a simple operation in a better accuracy.

THE BEST MODE FOR EMBODYING THE INVENTION

Below, the present invention is described in more detail by way of embodiments with reference to appended drawings.

Figure 1:
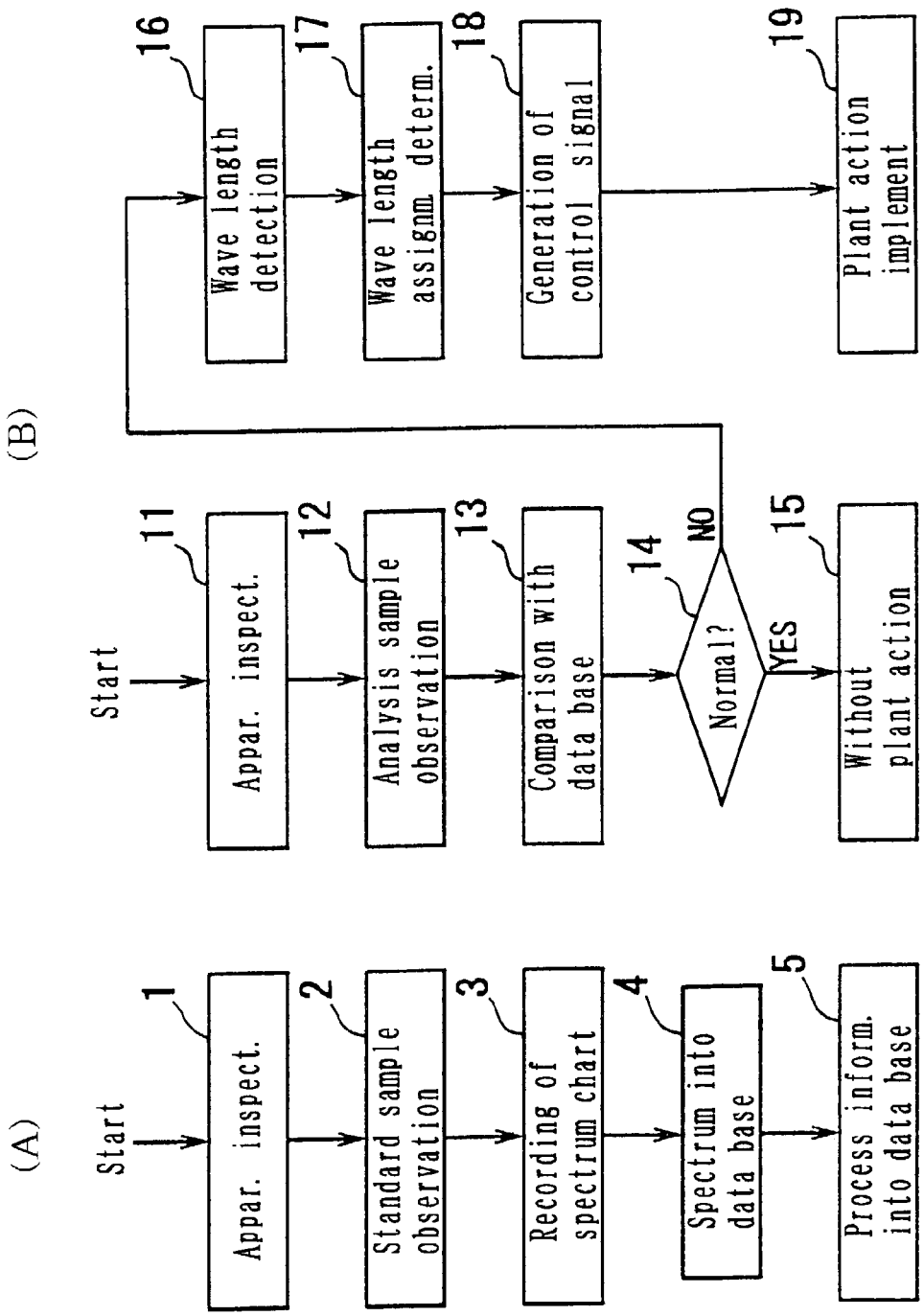
FIG. 1 is a flow diagram for one embodiment of the method for controlling the production processes according to the present invention with a near-infrared absorptiometry combined therewith.

In the flow diagram of FIG. 1 given for explaining an embodiment of the method for controlling production processes according to the present invention, (A) represents the flow sequence for constructing the data base and (B) indicates the flow sequence for the process control.

In constructing the data base as given in the sequence (A), inspection of the apparatus for the near-infrared absorptiometry is first carried out on step 1. Then, on step 2, a plurality of standard samples are observed by the near-infrared absorptiometry apparatus for a wave length range ranging from visible rays to near-infrared rays to obtain each absorption spectrum chart for each standard sample, whereupon, on step 3, the resulting spectrum charts are stored in a computer. The computer performs data processing of the stored absorption spectrum charts on step 4 for each of the selected wave lengths in order to determine the average standard absorbance intensity and standard deviation therefrom for each selected wave length, which are stored in the computer as data base for the process control. The construction of such data base is carried out by preparing each spectrum chart for a plurality of the standard samples for each kind of the product of, for example, product brand etc., and by sorting the obtained data as the data base for each kind. In the subsequent step 5, informations for the production process corresponding to the selected wave lengths are put in the data base. There may be inputted as the production informations, for example, the spectral change due to the variation of the near-infrared absorbance spectral characteristic features for the components, by-products and so on, as well as the control data.

In the sequence (B) for the process control, inspection of the apparatus for the near-infrared absorptiometry is first carried out on step 11. Then, on step 12, analysis samples taken from production process steps are examined for their absorbance spectra in the analysis range, which are then compared, on step 13, with those in the data base, in order to determine each deviation (analysis deviation) from the average standard intensity. When the analysis deviation is within the tolerance limit determined based on the standard deviation stored in the data base, the run is discriminated as normal and, if the analysis deviation is outside the tolerance limit, the run is discriminated as abnormal. Here, it is possible to compare the average of the observed results with the data in the data base for the analysis samples taken from process steps either simultaneously or each isolately at an interval by taking the average of the observed values, though the absorptiometry and the comparison may be performed for each analysis sample isolately. In case where the run is discriminated in the step 14 as normal, namely, if the absorbance intensities at the selected specific wave lengths are each within the tolerance limit prescribed in the data base of, for example, three times the standard deviation a of the absorbance intensity, the run is proceeded as such without any control action, as indicated in step 15.

In case where the run is discriminated on the step 14 as abnormal, namely, if the intensities at the selected specific wave lengths are each outside the tolerance limit prescribed in the data base of, for example, three times the standard deviation σ of the absorbance intensity, the wave length subject to such abnormal intensity is detected on step 16. This wave length and the production information are compared in step 17 with those in the data base, in order to find out what the control factor is, to which the wave length is assigned, such as a component, a material property or so on. Here, the abnormal intensity is examined as to whether it is greater than or smaller than the tolerance limit, whereby, on step 18, one or more controlling data for turning back the process step to normal run are obtained, from which one or more corresponding control signals are generated. The one or more control signals are inputted on step 19 in the production step to actuate one or more control operations as plant actions to effect control of the operation so as to obtain a product of manufacture of a quality within the tolerance limit. Here, the control operations may be performed either all at once or in a plurality of repetitions each over a brief time or, further, in a succeeding manner. After having been turned back to normal run, the production may be continued under the revised condition as such or the condition may be revised in accordance with each specific controlling data.

In the above process steps, the interval of the selected wave lengths may be 10 nm or less, preferably 2 nm or less. The wave length range of near-infrared rays ranges from 800 to 2,500 nm, so that the number of descriptive variables is calculated to be 1,700 when the interval is 1 nm, to be 850 when the interval is 2 nm and to be 170 when the interval is 10 nm. When, for example, the wave length range of 800–2,500 nm is divided by 2 nm, the selected wave length intervals, namely, the descriptive variables, are 850 in numbers. According to the present invention, the absorption spectra of plurality of standard samples in such selected wave length intervals are averaged and standard deviations are calculated, from which the data base is constructed.

The construction of data base for the standard samples is performed in the following way:

<<Recording of Standard Deviations for Each Wave Length Range in the Data Base>>

Standard deviation: $\sigma i = \{(1/N-1)\Sigma(X_i-\mu_i)^2\}^{1/2}$ in which N: number of observations Xi : intensity at each wave length μi: average intensity for N observations at each wave length (standard average intensity)

σi: standard deviation at each wave length (σi and μi for each wave length are recorded in the data base)

σ1, σ2, σ3, σ4 . . . σn

μ1, μ2, μ3, μ4 . . . μn

The comparison of the average of observed values at each wave length of analysis samples collected from production process steps with the data base is performed in the manner as follows:

Analysis deviation: Xi–μi (i: 1, 2, 3, . . . n)

in which xi: average intensity for N observations (analysis average intensity) at each wave length x1, x2, x3 , . . . xn μi: standard average intensity on the data base μi–μi: comparison of the analysis average intensity with the standard average intensity (analysis deviation)

x1–μ1, x2–μ2, x3–μ3, . . . xn–μn

Quotient of xi–μi by σi:

(xi–μi)/σi

Comparison of analysis deviation with tolerance limit:

if the tolerance limit=σ: $1 \geq (xi-\mu i)/\sigma i$ if the tolerance limit=2σ: $2 \geq (xi-\mu i)/\sigma i$ if the tolerance limit=3σ: $3 \geq (xi-\mu i)/\sigma i$ if the tolerance limit=4σ: $4 \geq (xi-\mu i)/\sigma i$ Atoms constituting a molecule are held under a symmetrical stretching vibration, a non-symmetrical stretching vibration and a deformation vibration. When a light of a frequency identical with that of the above vibration is irradiated onto the molecule, a part of the light is absorbed by the molecule, whereby it is excited from the ground state to an excited state. The excited atom emits lights of frequencies of harmonics of the absorbed infrared light, which can be detected in near-infrared region. Therefore, the detected near-infrared absorption wave length has a chemical attribute, so that pertinent wave lengths can be selected in accordance with the objective component. However, in practical analysis samples, there are in general few binary systems and they are present in most cases as multicomponent systems or as mixtures with multicomponent system or in a morphic state altered by reaction or polymerization.

Conserning the chemical attribute of absorption wave length, wave length ranges attributive to functional groups have been known and, based on this, the wave length ranges corresponding to the characteristic functional groups of the raw materials and the reaction products are put into a data base. Examples of the wave length ranges for functional groups are recited below:

| OH | 1st harmonics | 1345–1550 nm |
|---|---|---|
|  | 2nd harmonics | 910–1033 nm |
| NH | 1st harmonics | 1415–1516 nm |
|  | 2nd harmonics | 943–1010 nm |
| CH (aliphatic) | 1st harmonics | 1680–1760 nm |
|  | 2nd harmonics | 1120–1173 nm |
| CH (aromatic) | 1st harmonics | 1615–1665 nm |
|  | 2nd harmonics | 1077–1111 nm |

In the embodying mode given above, the spectrum chart, obtained by a near-infrared absorptiometer, of the reaction product in a reaction system is processed by differentiation-treatment, from which a second derivative curve is obtained in the wave length range of 800–2,500 nm. The average spectrum is compared with the average spectrum recorded in the data base to compare with the data base of functional groups for the wave lengths and wave length ranges, at or for which the standard deviation is exceeded in plus or minus level. The raw material, reaction product or so on is specified thereby and control of the plant is effected via a computer so as to maintain within the definite standard deviation.

It has been known that the absorbance of spectrum obtained by near-infrared observation suffers from shifting of the baseline due to external condition of, for example, temperature, water content, flow velocity and so on. This means that the absorbance value may be varied by such baseline shifting (alteration in the absorbance) when the originally obtained spectrum is used as such, whereby considerable influence on the observation results should be taken into account. Such an influence of the baseline shifting can be suppressed by processing the original spectrum chart by differentiating it, whereby a steady derivative curve of the spectral absorption intensity chart can be obtained.

When an absorption spectrum chart is processed by differentiating it, high frequency noises are magnified (emphsized) and may participate in the control action erroneously as if they represent near-infrared informations. Therefore, it is essential for the requisite performance of a near-infrared absorptiometer that the noise level should be at the highest $50 \times 10^{-6}$ absorbance units.

Sigma discrimination method is a technique for discriminating as to whether or not a product on production corresponds to a previously obtained rated brand product, wherein identical quality product can be sorted statistically within a deviation of 3σ at a probability of 99.7%. Here, 20 to 30 samples of differentiation curves of the near-infrared absorption spectrum charts of each brand approved to be rated product are selected for constructing the data base, with which that of the process product on production is compared. If the deviation exceeds the range of 3σ, namely three times the standard deviation (σ) of the standard spectrum used as the base, in the wave length range of 800–2,500 nm, the process product is judged as being extra-rated.

In the process control, near-infrared spectral charts obtained at a constant interval are inputted in a near-infrared system constructed from a near-infrared absorptiometer, a computer for controlling the near-infrared absorptiometer and a data analyzing computer, by differentiating the spectral charts directly in the data analyzing computer or via the controlling computer, whereupon the quantitative analysis value and the 3σ value are displayed simultaneously or solely of one of them on a CRT.

Below, the present invention will be described by way of Examples.

EXAMPLE 1

EXAMPLE 1 describes an embodiment of controlling production process of a polyolefin resin. In the process, an olefinic monomer comprising 4-methyl-pentene-1 is polymerized in the presence of a catalyst to produce a polyolefin resin.

Figure 2:
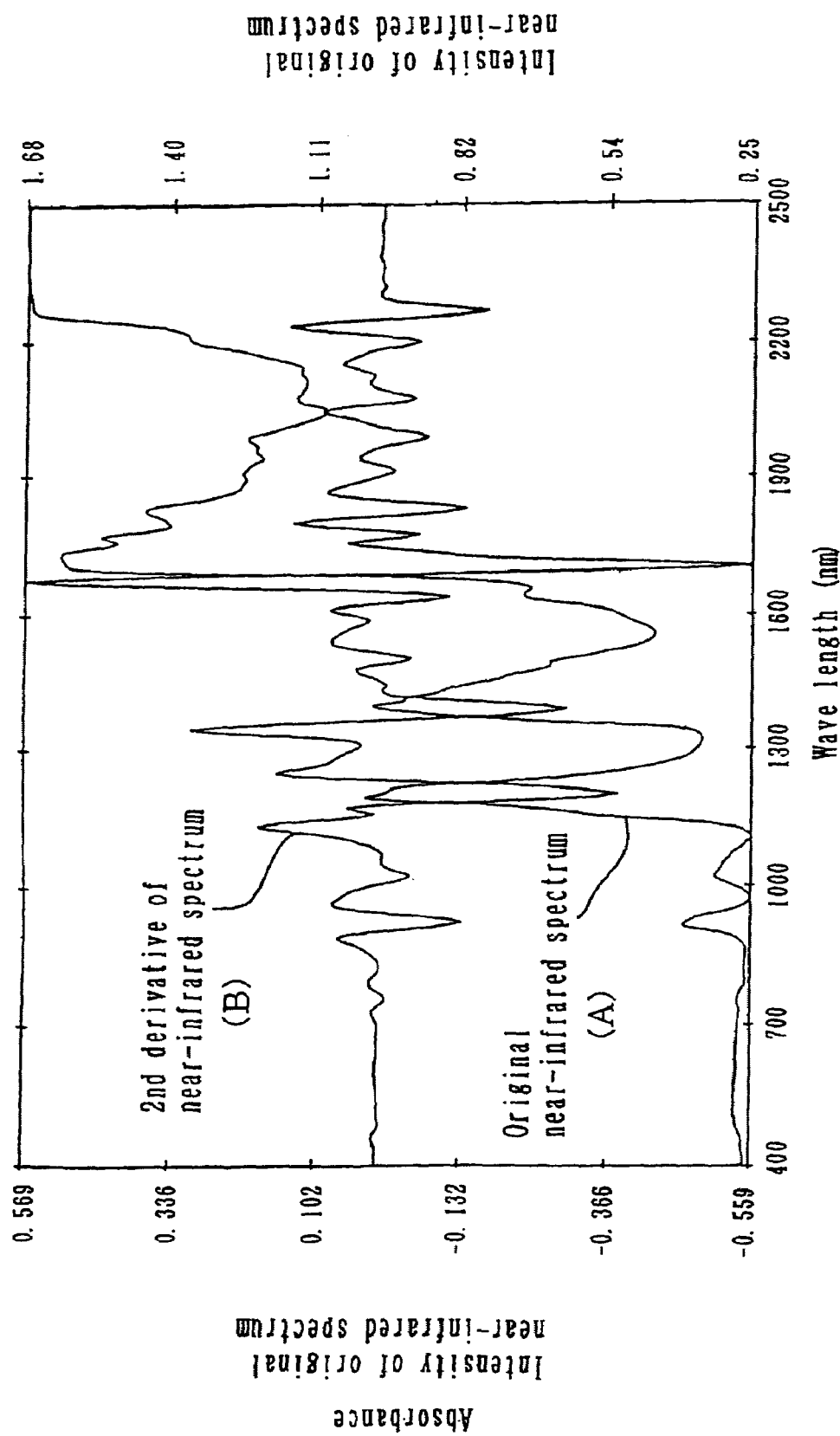
FIG. 2 is a near-infrared absorption spectrum chart for a standard sample of EXAMPLE 1.
Figure 3:
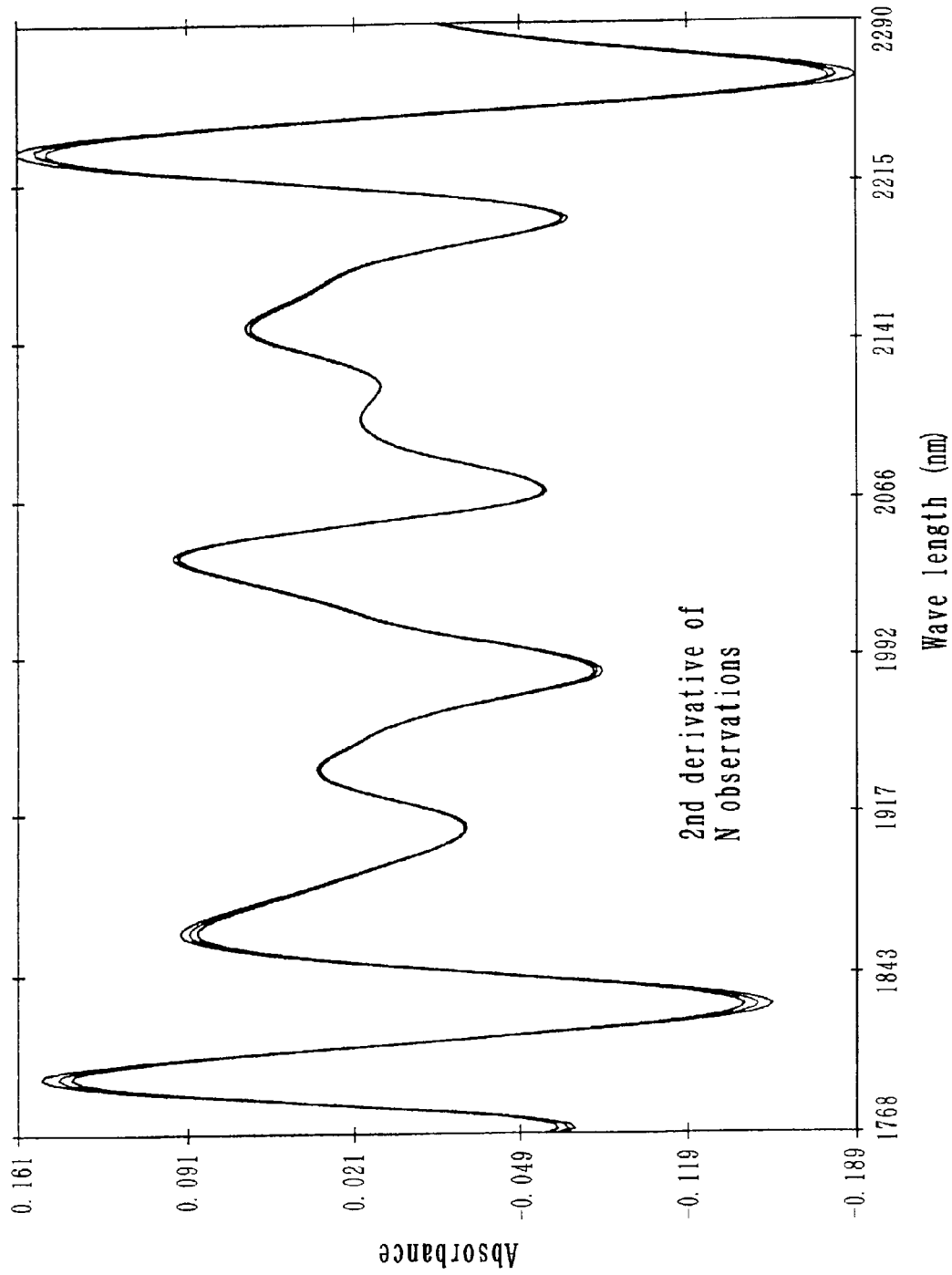
FIG. 3 shows the second derivative curves of the near-infrared absorption spectrum charts for a plurality of standard samples of EXAMPLE 1.
Figure 4:
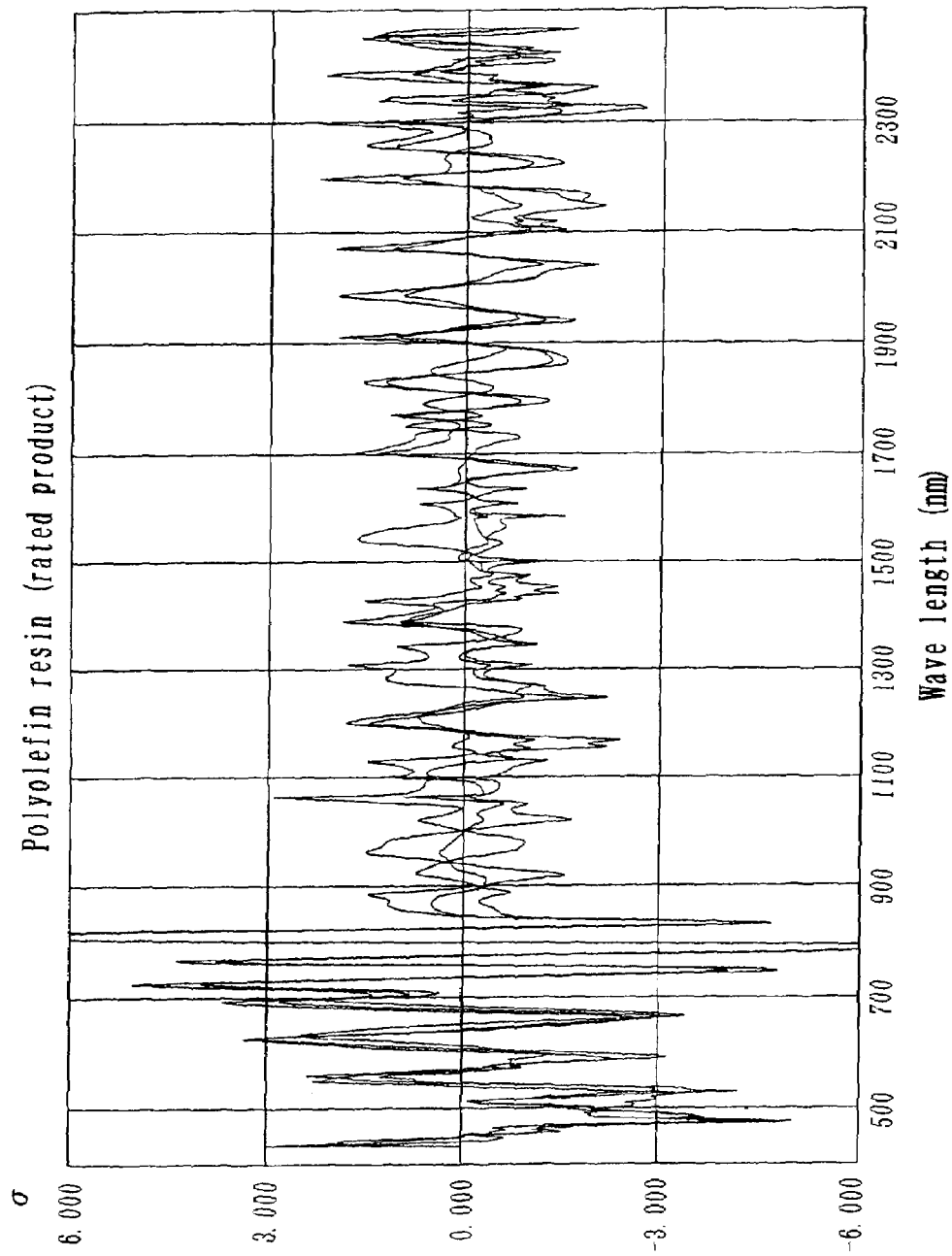
FIG. 4 shows the second derivative curves of the near-infrared absorption spectrum charts for several analysis samples in normal run of EXAMPLE 1.

FIG. 2 shows a near-infrared absorption spectrum chart of a standard sample of a product judged as a rated product by conventional chemical analysis, in which the curve (A) represents the original absorption spectrum chart and the curve (B) represents second derivative curve in which the original spectral chart is doubly differentiated. The original spectrum chart (A) shows a baseline shifting on the side of longer wave length and overlapped peaks, whereas the curve (B) exhibits a flattened horizontal baseline and isolately appearing emphasized absorption peaks. FIG. 3 shows the fluctuation width of the second derivative curves of the spectrum charts observed for a plurality of standard samples (20 samples in this EXAMPLE). FIG. 4 shows second derivative curves for a plurality of analysis samples (3 samples) collected from production process steps, in which a data base is constructed by data-processing the second derivative curves obtained in FIGS. 1 and 2 to produce the average intensity for selected wave lengths selected at an interval of 2 nm and standard deviations thereof, whereupon the horizontal line of level 0.000 is settled at the average intensity level and the horizontal lines of levels ±3.000 are settled at the levels three times standard deviation $\sigma$, namely $3\sigma$. FIG. 4 corresponds to the case where the production process is in normal operation, wherein the product information, such as the composition and the material properties of the analysis samples and so on, are included in the spectrum in the range of 800–2,500 nm. All the peaks in the range of 800–2,500 nm for the analysis samples lie within the range of $3\sigma$, namely, they are within the tolerance limit. The spectrum below 850 nm falls under visible ray region and includes information concerning color of the analysis sample, which are permitted to exceed the range of $3\sigma$.

Figure 5:
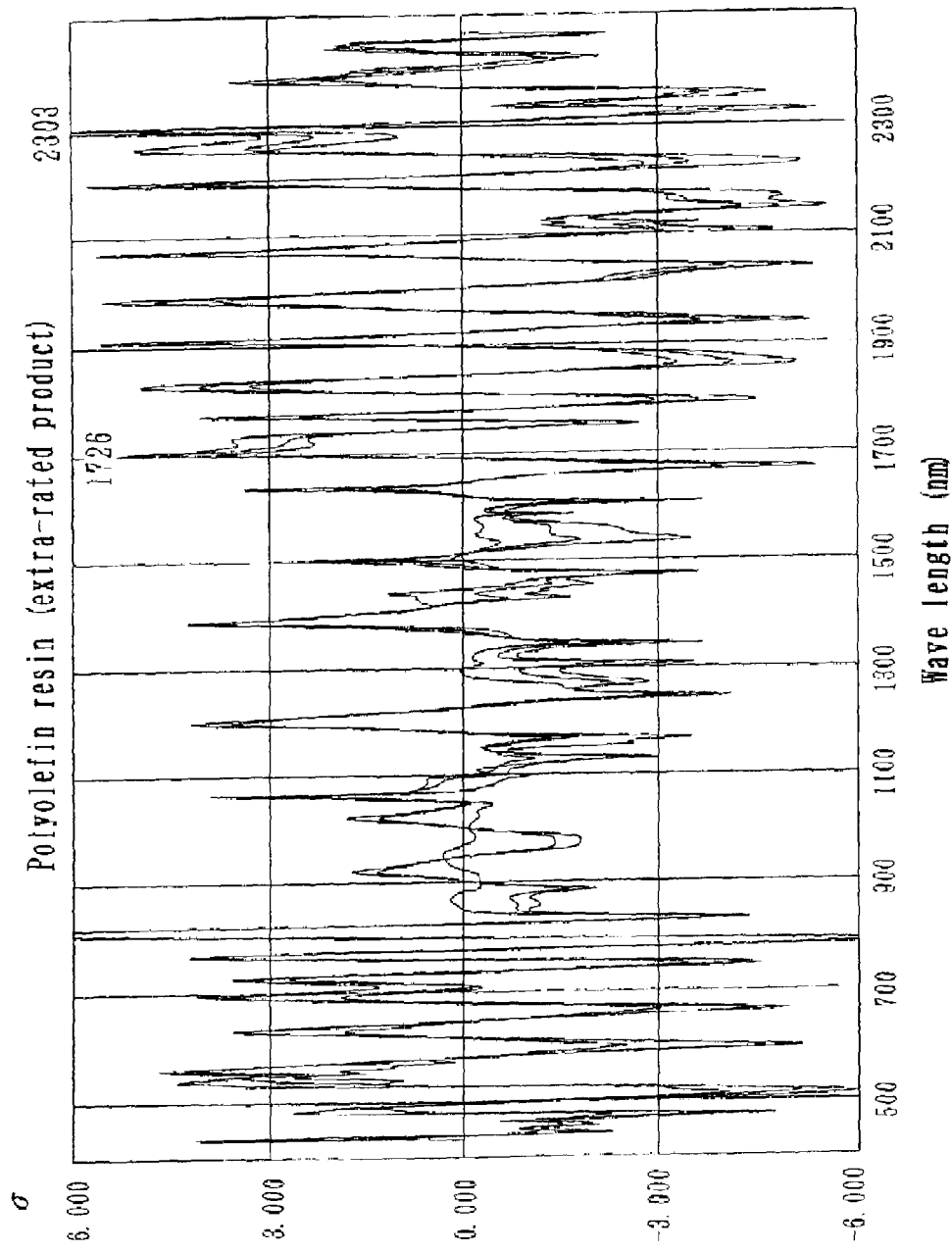
FIG. 5 shows the second derivative curves of the near-infrared absorption spectrum chart for several analysis samples in an abnormal run of EXAMPLE 1.
Figure 6:
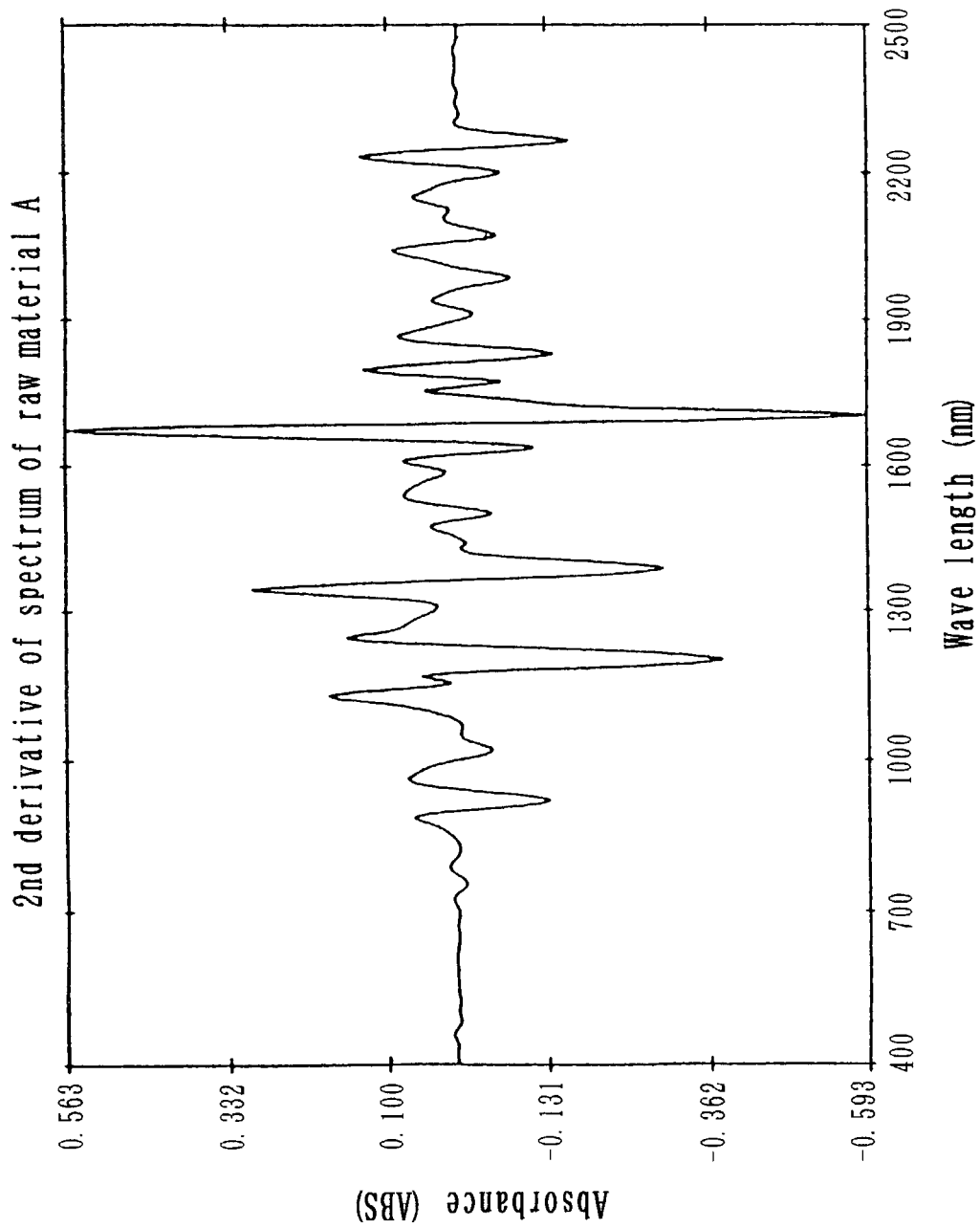
FIG. 6 shows the second derivative curve of the near-infrared absorption spectrum chart for the raw material A.
Figure 7:
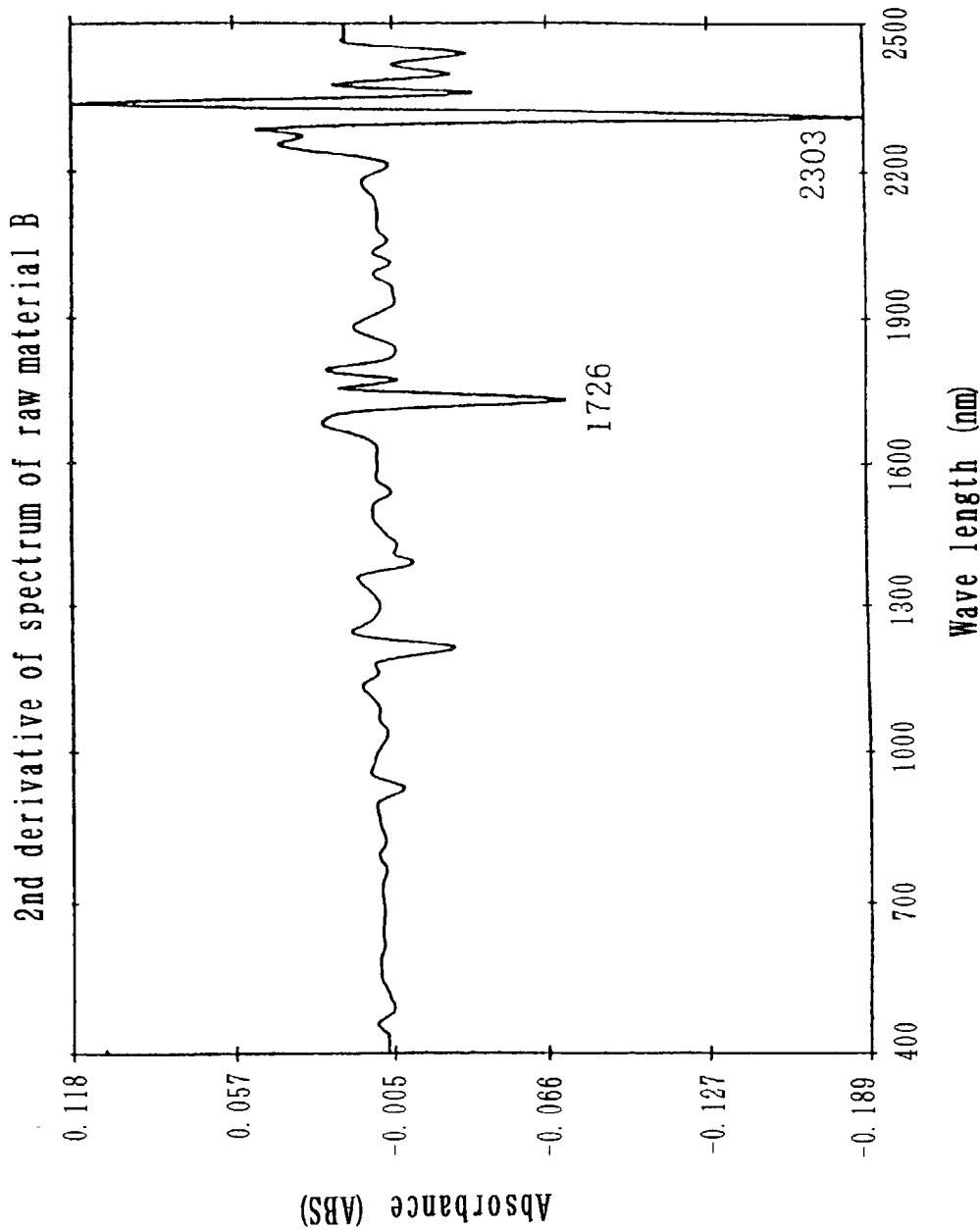
FIG. 7 shows the second derivative curve of the near-infrared absorption spectrum chart for the raw material B.
Figure 8:
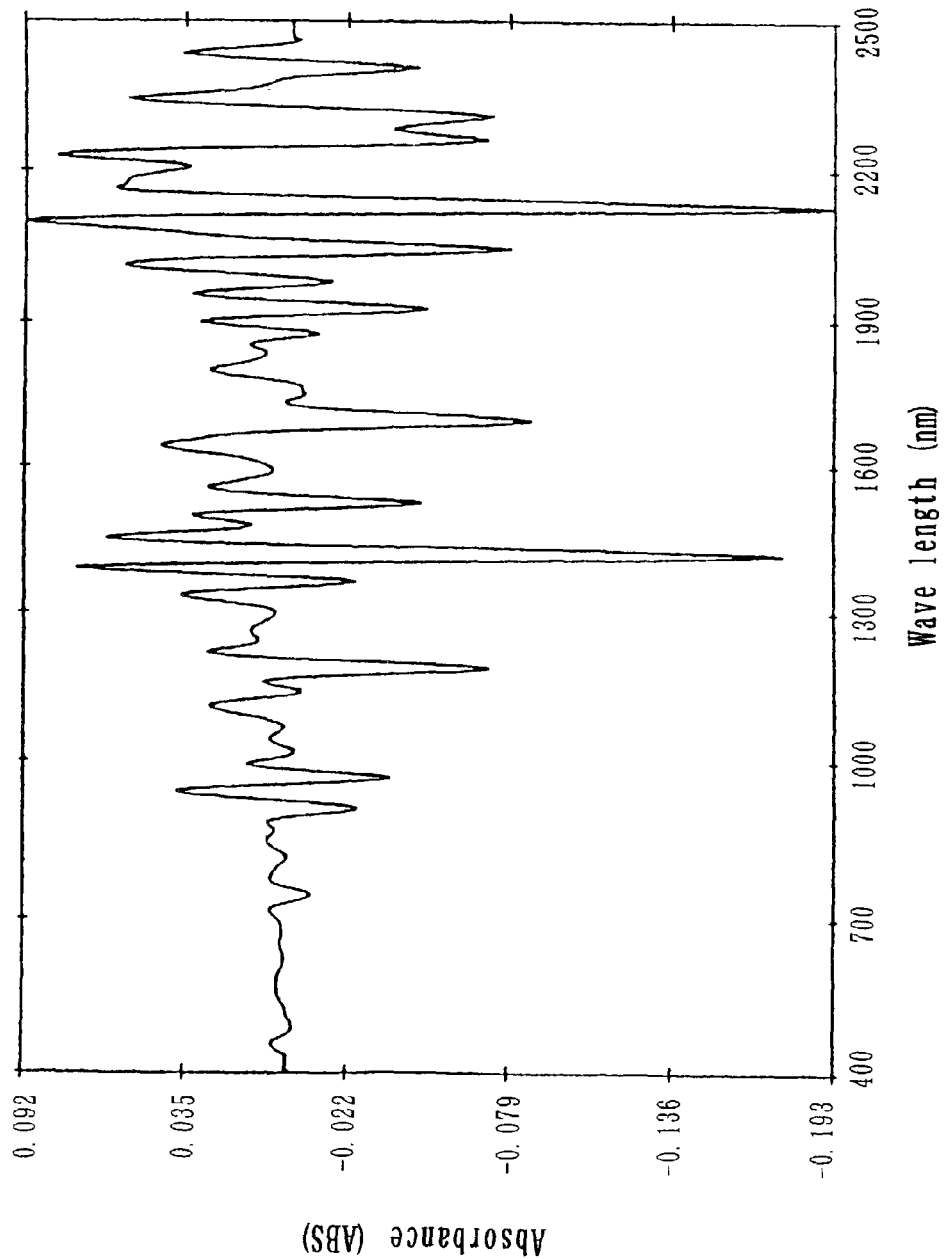
FIG. 8 shows the second derivative curve of the near-infrared absorption spectrum chart for the raw material C.

FIG. 5 indicates the case of operation where abnormal values appear and shows the second derivative curves for the analysis samples collected from production process steps similar to those of FIG. 4. Many of the peaks in the range of 800–2,500 nm are outside the value $3\sigma$, namely abnormal values. FIGS. 6, 7 and 8 show each the second derivative curve of the spectrum chart for the raw material (A), raw material (B) and raw material (C), respectively, which are put in a data base as production information. When comparing the spectrum of FIG. 5 with respect to the peaks at 1726 nm and 2303 nm, at which the values exceed $3\sigma$, with the data base of production information, they coincide with those of component (B) of FIG. 7, indicating that the component (B) is excessive. Therefore, a control signal for decreasing the amount of component (B) was given off, whereby the production process was turned back to normal operation. When the peaks exceeding $3\sigma$ were originated from an impurity, the control was able to be realized by emitting a signal for diminishing such impurity.

EXAMPLE 2

Figure 9:
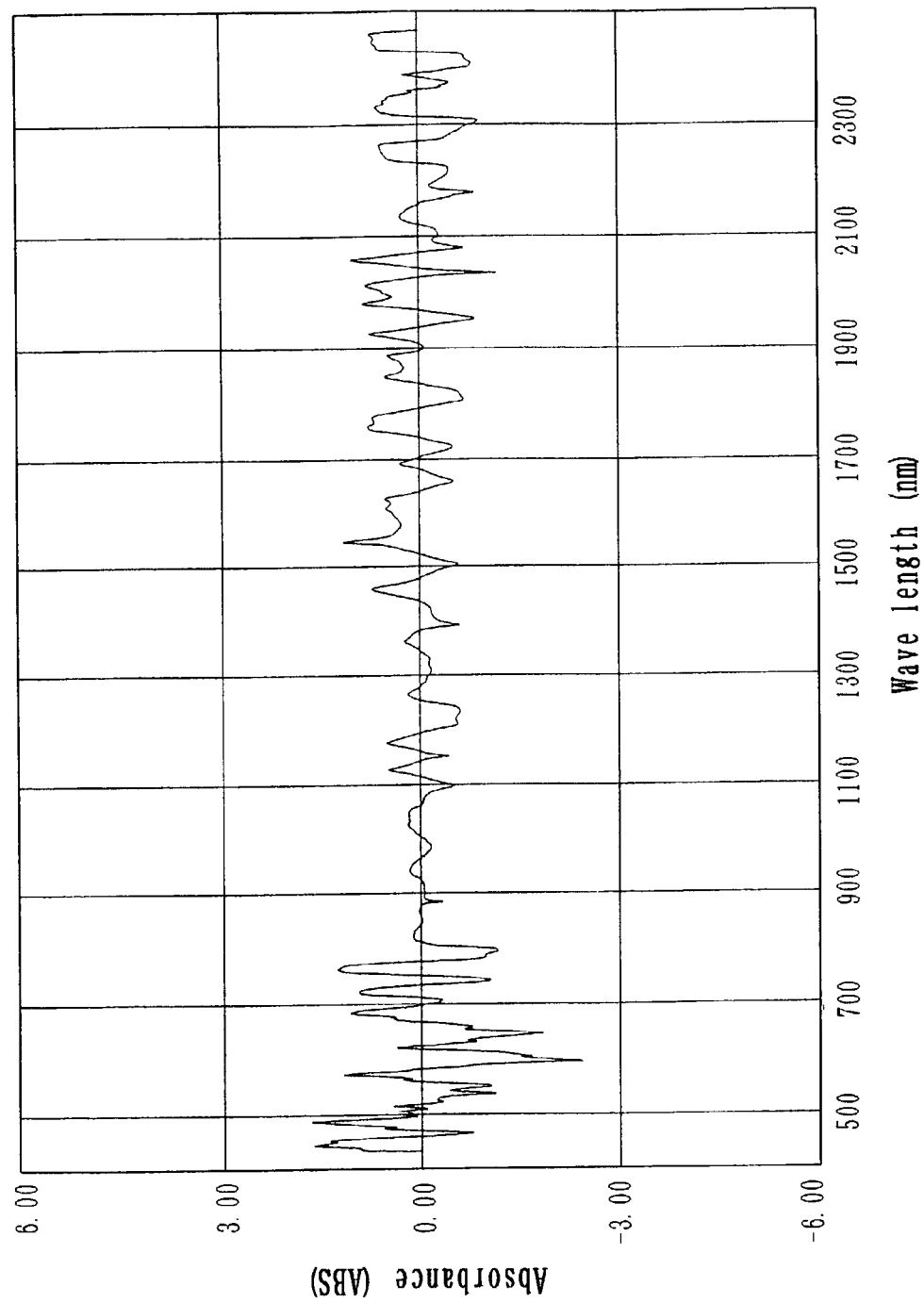
FIG. 9 shows data-processed chart of the second derivative curve of the near-infrared absorption spectrum chart for an analysis sample in normal run of EXAMPLE 2.

EXAMPLE 2 describes an embodiment of controlling the process for producing a polyester resin. In this production process, a polyester resin, such as polyethylene terephthalate or so on, is produced via an esterification step, in which a dicarboxylic acid product composed mainly of terephthalic acid is reacted with a diol product composed mainly of ethylene glycol, and a polycondensation step. FIG. 9 concerns an embodiment in which discrimination was effected for the polyester resin using a data base made from the second derivative curve of a near-infrared spectrum chart obtained using a plurality of production products which had been judged by conventional chemical analysis to be rated ones, by assuming a threshold value of $3\sigma$ wherein the production was carried out under normal operation. There is no wave length range with peaks exceeding the range of $3\sigma$ in the near-infrared region, so that the product can be judged as comparable to the rated product.

Figure 10:
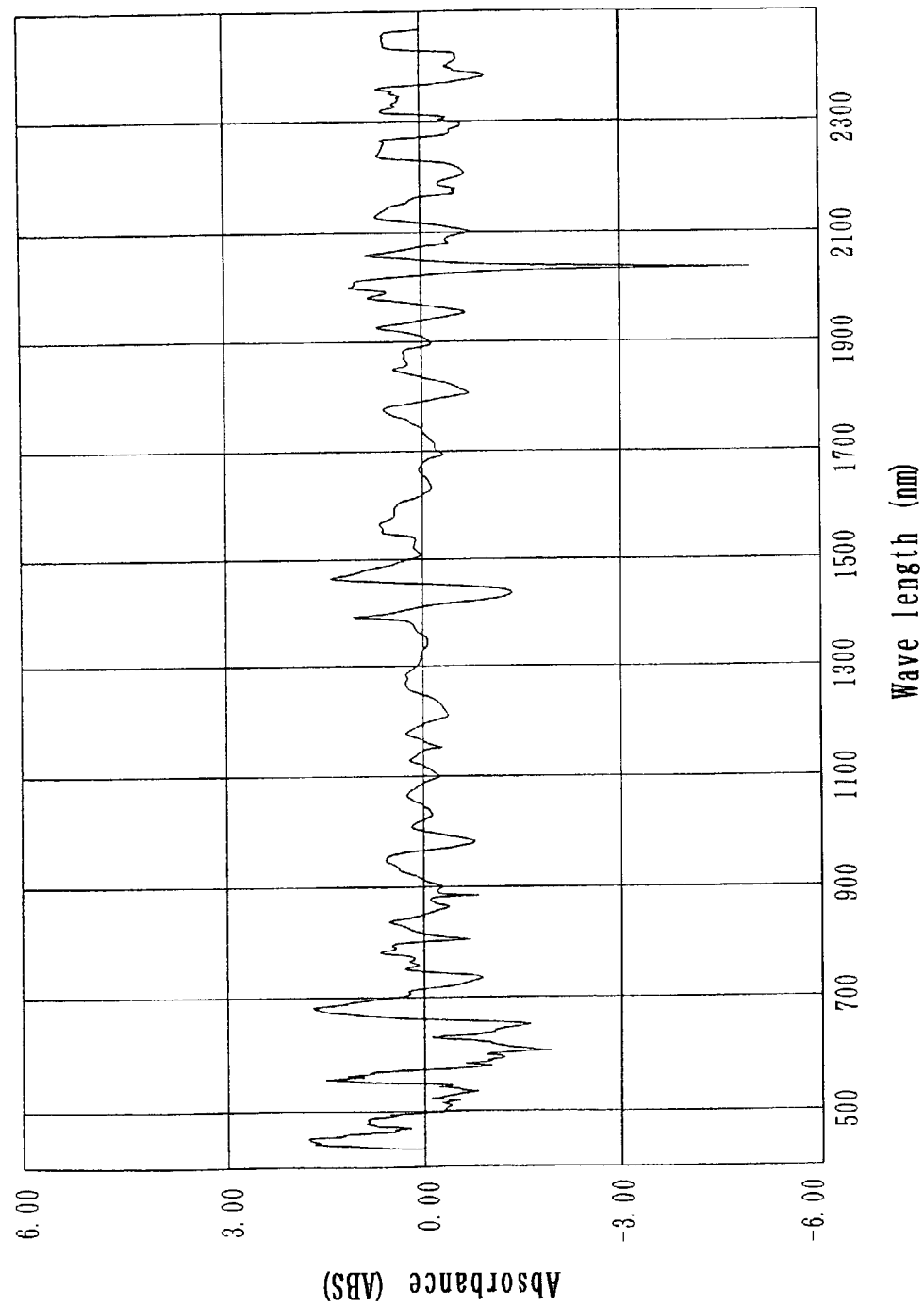
FIG. 10 shows data-processed chart of the second derivative curve of the near-infrared absorption spectrum chart for an analysis sample in abnormal run of EXAMPLE 2.

FIG. 10 concerns an embodiment in which discrimination was effected for the polyester resin using a data base made from the second derivative curve of a near-infrared spectrum chart obtained using a plurality of production products which had been judged by conventional chemical analysis to be rated ones, by assuming a threshold value of $3\sigma$, wherein the production was carried out under operation ascribable to abnormal values. In the near-infrared region, a wave length at which $3\sigma$ value is exceeded (at 2034 nm) can be recognized. The absorbance at 2034 nm corresponds to the characteristic absorption band attributive to the influence on the product color. On detecting an excess of the $\pm 3\sigma$ threshold, the production process was operated so as to alter the stabilizer feed rate. The component of diethylene glycol in the polyester resin has a characteristic absorption band around 1224 nm. When this band exceeded the threshold value of $\pm 3\sigma$, the production was operated under alteration of the polycondensation condition so as to vary the amount of diethylene glycol formed (formed spontaneously), whereby normal product was regained. Here, it was necessary to operate the production process by altering the condition of polycondensation or by supplementing diethylene glycol monomer, when the threshold value of $-3\sigma$ was exceeded.

Similarly, there is a characteristic absorption band at 1710–1538 nm as to the IV value (Inherent Viscosity value). When the IV value exceeded $\pm 3\sigma$, it was necessary to carry out the operation so as to lower the level in the polymerization reactor or so as to decrease the flow rate of the heating gas (inert gas) or so as to reduce the temperature of the preheating phase of solid phase polymerization, whereas when $-3\sigma$ was exceeded, it was necessary to carry out the operation in the manner reverse to the above.

EXAMPLE 3

This example concerns an embodiment of controlling process steps in the production of phenols.

The production process comprises a cleavage step in which phenols are formed by a cleavage reaction from a hydroperoxide in an organic solvent using an acid at lower concentration. Here, the items to be administrated comprises concentrations of residual hydroperoxide, sulfuric acid, water, phenol, hydroquinone and so on, which have each a correlation with the characteristic features as follows:

| | |
|---|---|
| Residual hydroperoxide | reaction efficiency and safety |
| Water | product yield and reaction velocity |
| Sulfuric acid | product yield and safety |
| Phenol | yield and reaction efficiency |

Figure 11:
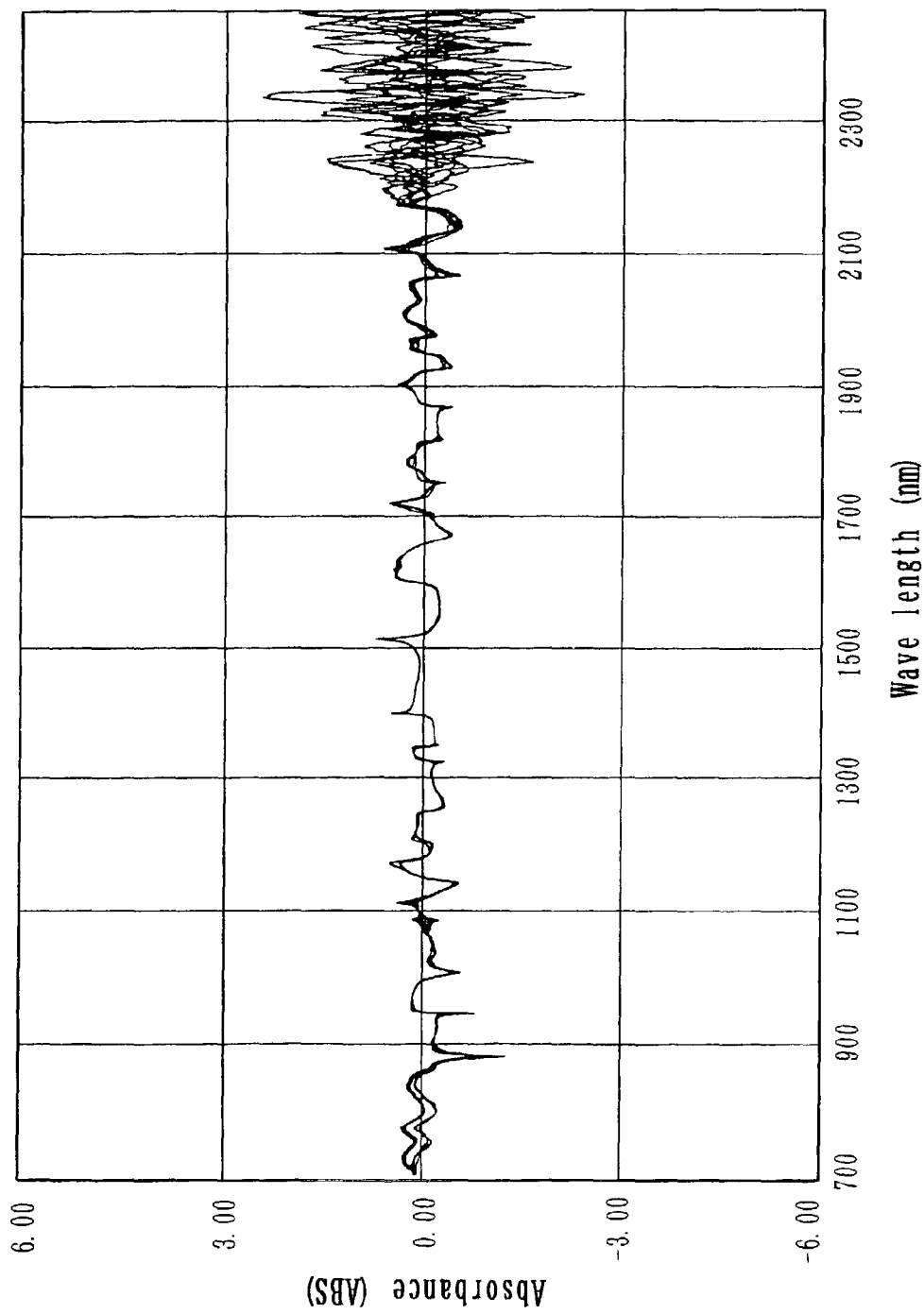
FIG. 11 shows data-processed chart of the second derivative curve of the near-infrared absorption spectrum chart for an analysis sample in normal run of EXAMPLE 3

FIG. 11 concerns an embodiment in which discrimination was effected for the product of cleavage step using a data base made from the second derivative curve of a near-infrared spectrum chart obtained using a plurality of cleavage step products which had been judged by conventional chemical analysis to be within the operation administration range, by assuming a threshold value of $3\sigma$, wherein the production was carried out under normal operation. There is no wave length range in which $3\sigma$ is exceeded in the near-infrared region, so that the operation state can be judged as normal.

Figure 12:
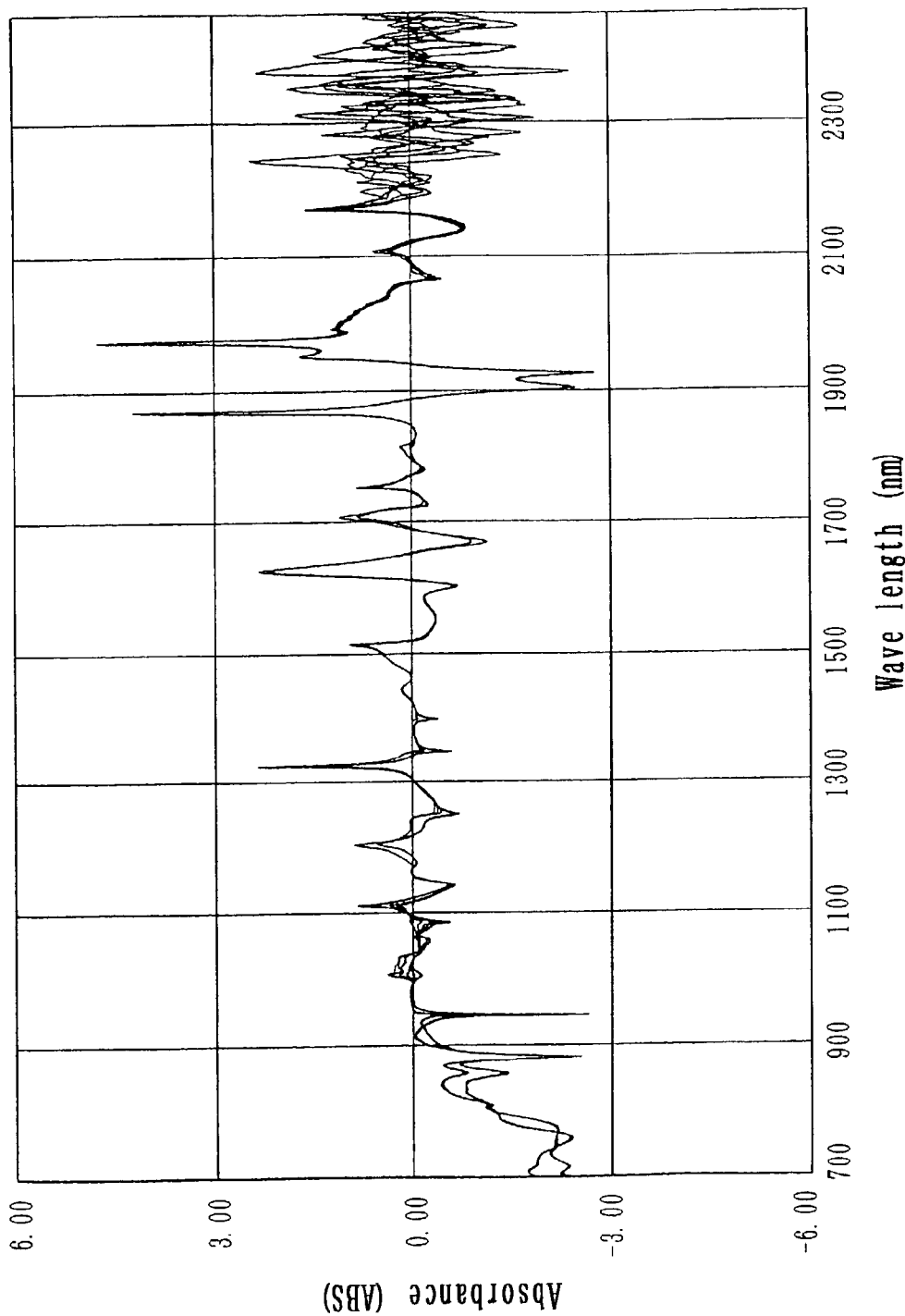
FIG. 12 shows data-processed chart of the second derivative curve of the near-infrared absorption spectrum chart for an analysis sample in abnormal run of EXAMPLE 3.

FIG. 12 concerns an embodiment in which discrimination was effected for the product of cleavage step using a data base made from the second derivative curve of a near-infrared spectrum chart obtained using a plurality of cleavage step products which had been judged by conventional chemical analysis to be without the operation administration range, by assuming a threshold value of $3\sigma$, wherein abnormality appeared. In the near-infrared region, a wave length at which $3\sigma$ range is exceeded (at 1978 nm) can be recognized. The absorbance at 1978 nm corresponds to the characteristic absorption band attributive to the hydroperoxide. When the threshold value of $\pm 3\sigma$ was exceeded, normal state was able to be regained by operating under alteration of the amount of supplied sulfuric acid. The absorption band lies at 2036 nm for sulfuric acid, 1900 and 1400 nm for water and 1930 nm for phenol. When the values for them exceeded the above threshold value, the normal state was able to be regained by altering the feed amounts of them.

INDUSTRIAL APPLICABILITY

In the process steps of production of products of manufacture, such as chemical products, foods and others, the production process is controlled so as to maintain normal operation state by performing the control in such a way that analysis samples collected from the raw materials, solvent, water, intermediate products, product of manufacture, by-products and so on are analyzed by near-infrared absorptiometry to obtain observed values for these components and material properties and the control is effected so as to maintain these observed values each at a predetermined value.

The invention claimed is:

1. A method for controlling a production process without having to resort to the preparation of a calibration curve for predicting data for analysis samples, the method comprising
taking an absorbance spectrum for each of a plurality of standard samples collected from a production process step in an analysis range including near-infrared region,
constructing a data base from a differentiation curve of a near-infrared spectrum chart obtained using a plurality of production products that had been judged by conventional chemical analysis to be rated products, by calculating standard deviations and the average intensity of the standard samples (standard average intensity) in respect of each of the wave lengths selected from the spectrum included in the said analysis range at a constant interval,
taking an absorbance spectrum in the said analysis range for each analysis sample collected from the production process step and comparing the resulting absorbance spectrum with the data base,
estimating the deviation (analysis deviation) of the intensity of the absorbance spectrum of each of the analysis samples (analysis intensity) at each of the said selected wave lengths from the standard average intensity,
comparing, when the absorbance spectrum includes wave length(s) at which the analysis deviation of the absorbance of the analysis sample is outside a tolerance limit determined based on the standard deviation, the wave length showing the analysis deviation of the absorbance outside the tolerance limit with production information given preliminarily in the data base in order to find out one or more control factors responsive to said analysis deviation of absorbance of the analysis sample,
estimating control data for reclaiming the production process based on the one or more control factors, and
controlling the production process so as to obtain production product within the said tolerance limit by inputting the said control data to the production process step.

2. The method as claimed in claim 1, wherein the production information stored in the data base are those of the component material corresponding to the said selected wave lengths.

3. The method as claimed in claim 2, wherein the deviations (analysis deviations) of the analysis intensities from the standard average intensity are discriminated as to whether or not they are within the tolerance limit determined based on the standard deviations given in the data base for the standard samples.

4. The method as claimed in claim 3, wherein the said analysis range is from 400 nm to 2,500 nm.

5. The method as claimed in claim 4, wherein the said analysis range is from 800 nm to 2,500 nm.

6. The method as claimed in claim 5, wherein the selected wave lengths have an interval of 10 nm or less.

7. The method as claimed in claim 6, wherein the selected wave lengths have an interval of 2 nm or less.

8. The method as claimed in claim 7, wherein the absorbance spectrum is processed by differentiation for the analysis samples.

9. The method as claimed in claim 8, wherein the absorbance spectrum is processed by building up the second derivative thereof.

10. The method as claimed in claim 9, wherein the data base is constructed from a plurality of standard samples of a plurality of kinds, by calculating the standard average intensity and standard deviations for each kind.

11. The method as claimed in claim 10, wherein absorbance spectra are obtained for a plurality of the analysis samples and estimating the deviations of average intensities of the analysis samples (analysis average intensity) at the selected wave lengths from the standard average intensity.

12. The method as claimed in claim 1, wherein the deviations (analysis deviations) of the analysis intensities from the standard average intensity are discriminated as to whether or not they are within the tolerance limit determined based on the standard deviations given in the data base for the standard samples.

13. The method as claimed in claim 1, wherein the said analysis range is from 400 nm to 2,500 nm.

14. The method as claimed in claim 13, wherein the said analysis range is from 800 nm to 2,500 nm.

15. The method as claimed in claim 1, wherein the selected wave lengths have an interval of 10 nm or less.

16. The method as claimed in claim 15, wherein the selected wave lengths have an interval of 2 nm or less.

17. The method as claimed in claim 1, wherein the absorbance spectrum is processed by differentiation for the analysis samples.

18. The method as claimed in claim 17, wherein the absorbance spectrum is processed by building up the second derivative thereof.

19. The method as claimed in claim 1, wherein the data base is constructed from a plurality of standard samples of a plurality of kinds, by calculating the standard average intensity and standard deviations for each kind.

20. The method as claimed in claim 1, wherein absorbance spectra are obtained for a plurality of the analysis samples and estimating the deviations of average intensities of the analysis samples (analysis average intensity) at the selected wave lengths from the standard average intensity.

* * * * *